United States Patent [19]
Crainich

[11] Patent Number: 5,344,061
[45] Date of Patent: Sep. 6, 1994

[54] RATCHET ASSEMBLY FOR MEDICAL INSTRUMENT

[76] Inventor: Lawrence Crainich, Ceda Rd., Charlestown, N.H. 03603

[21] Appl. No.: 100,983

[22] Filed: Aug. 3, 1993

[51] Int. Cl.⁵ .................................... A61B 17/068
[52] U.S. Cl. .................................... 227/182; 227/19; 81/313; 74/575; 74/577 M; 74/578; 74/557
[58] Field of Search .................... 227/19, 182, 67; 81/313; 74/575, 578, 557, 577 M

[56] References Cited

U.S. PATENT DOCUMENTS

| | | | |
|---|---|---|---|
| 580,556 | 4/1897 | Reinhold | 81/313 |
| 2,481,012 | 9/1949 | Haseltine | 74/578 |
| 2,737,070 | 3/1956 | Dibner | 81/313 |
| 2,959,993 | 11/1960 | Freimark | 81/313 |
| 3,101,017 | 8/1963 | Malkin et al. | 81/313 |
| 3,456,516 | 7/1969 | Fisnar et al. | 74/575 |
| 4,425,915 | 1/1984 | Ivanov | 227/19 |
| 4,448,194 | 5/1984 | DiGiovanni et al. | 227/67 |
| 4,951,860 | 8/1990 | Peters et al. | 227/19 |

*Primary Examiner*—Scott Smith
*Attorney, Agent, or Firm*—Bachman & LaPointe

[57] ABSTRACT

A ratchet assembly for a medical instrument having a handle and a trigger member for operating the medical instrument, the trigger member being movable relative to the handle between a first position and a second position and being biased by a biasing member toward the first position, the ratchet assembly comprising a rack disposed in the handle, an engagement member for engaging the rack, slidably disposed in the handle relative to the rack and connected to the trigger member so that displacement of the trigger member slides the engagement member relative to the rack, the engagement member being biased into engagement with the rack so that, as the trigger is displaced from the first position to the second position, the engagement member engages the rack in a plurality of positions so as to hold the trigger member at a desired point between the first position and the second position against the biasing member, and a cam member, arranged in the handle, for disengaging the engagement member from the rack when the trigger member is displaced to the second position, and for reengaging the engagement member with the rack when the trigger member is returned to the first position from the second position.

18 Claims, 4 Drawing Sheets

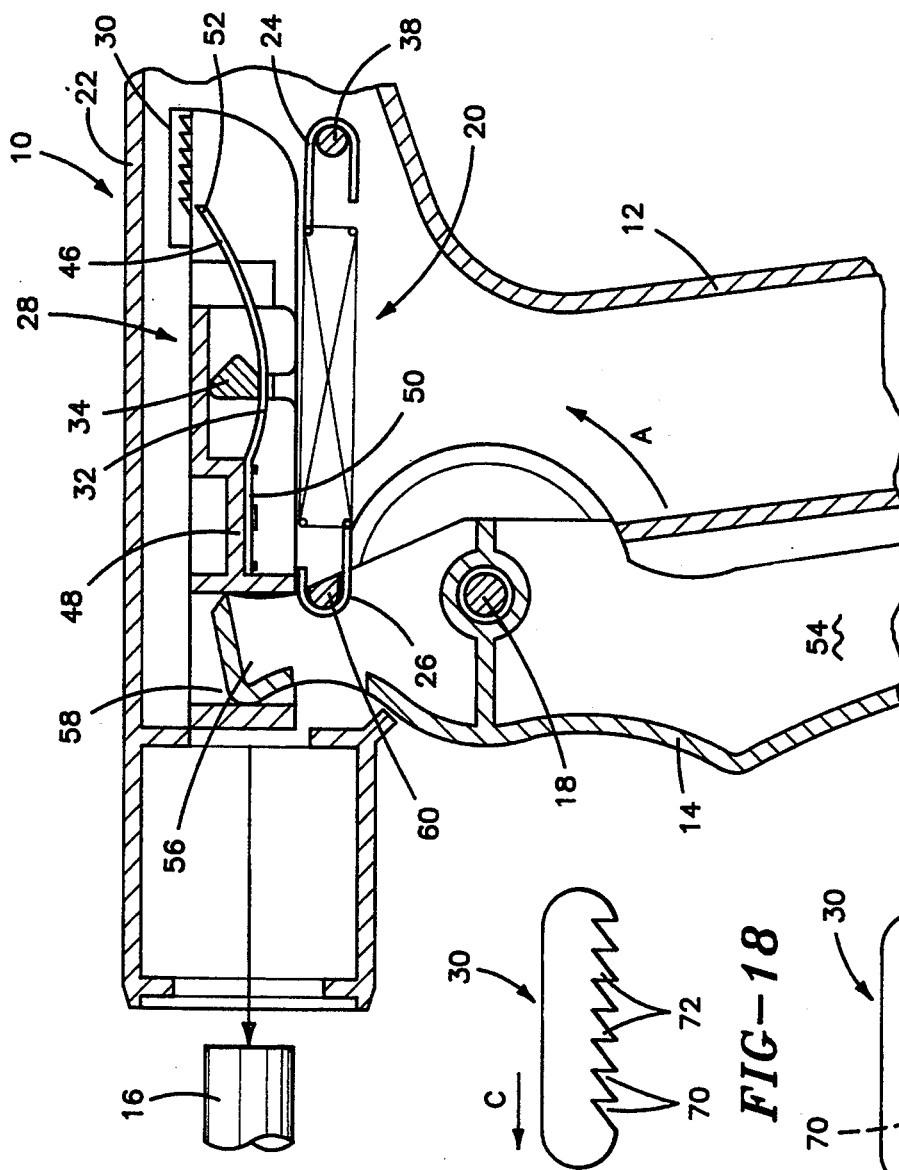

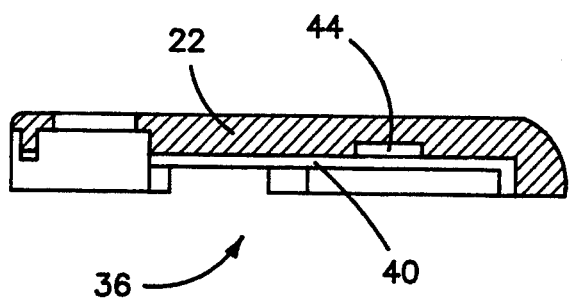
*FIG-3*
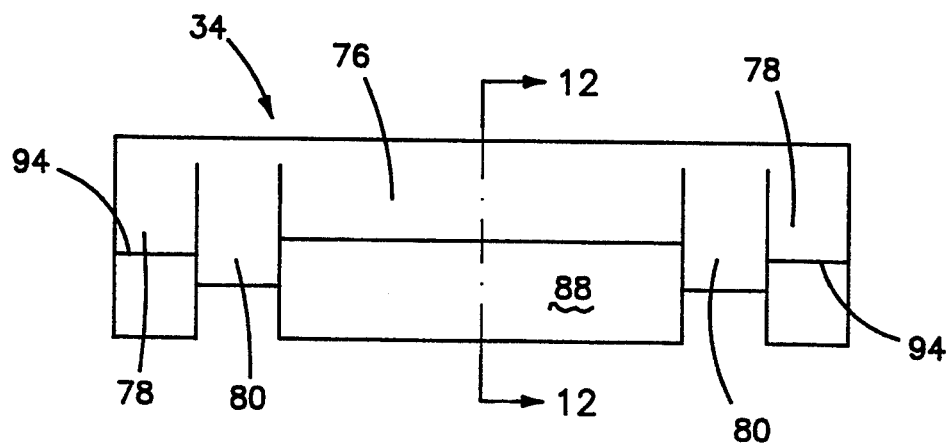
*FIG-11*
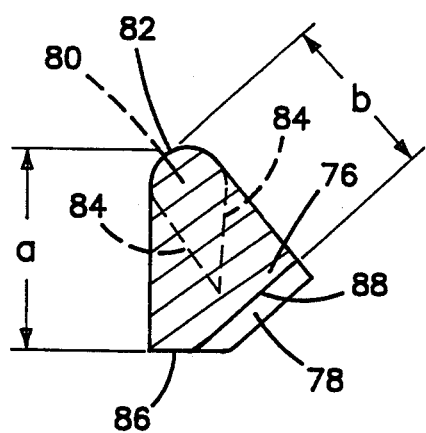 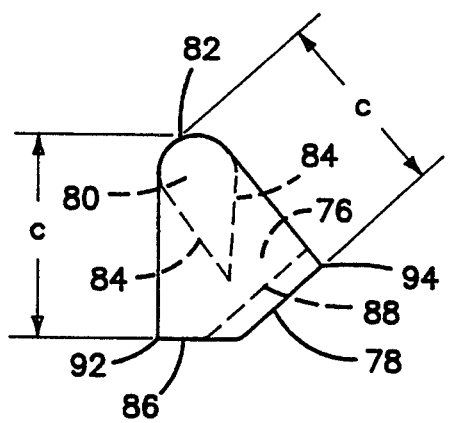
*FIG-12*  *FIG-13*

1

RATCHET ASSEMBLY FOR MEDICAL INSTRUMENT

BACKGROUND OF THE INVENTION

The invention relates to medical instruments and, particularly, to a ratchet assembly for such a medical instrument, especially for a surgical stapler.

Numerous medical instruments exist which are operated by a trigger or switch member or the like which pivots or slides relative to a handle of the instrument. Such operation of the trigger member typically operates the instrument for its intended function.

Typically, it is desirable to perform the pivot or movement of the trigger member and, thus, the operation of the instrument, in a step wise manner. It is desirable to provide such an instrument wherein such stepwise operation is facilitated.

It is further desirable to provide such an instrument wherein the trigger member readily returns to its initial position relative to the handle after the trigger member has been fully depressed, pivoted, or otherwise actuated so as to prepare for the next operation of the instrument.

It is thus the principal object of the invention to provide a ratchet assembly for a medical instrument which provides a smooth and reliable ratcheting or stepwise operation of the trigger member relative to the handle of the device.

It is a further object of the invention to provide such an assembly wherein the increment from step to step of the ratchet operation is small so as to provide small incremental steps and thereby accurate operation of the instrument.

A still further object of the invention is to provide such an apparatus wherein the trigger member is readily returned to the initial position after reaching a fully operated position.

Other objects and advantages will appear hereinbelow.

SUMMARY OF THE INVENTION

The present invention readily attains the foregoing.

According to the invention, a ratchet assembly is provided which provides a ratchet operation of a trigger member of a medical instrument between a first position of the trigger member relative to the handle of the instrument and a second position of the trigger member relative to the handle.

The ratchet assembly comprises: a rack disposed in the handle, an engagement member for engaging the rack, slidably disposed in the handle relative to the rack and connected to the trigger member so that displacement of the trigger member slides the engagement member relative to the rack, the engagement member being biased into engagement with the rack so that, as the trigger is displaced from the first position to the second position, the engagement member engages the rack in a plurality of positions so as to hold the trigger member at a desired point between the first position and the second position against the biasing member, and cam means, arranged in the handle, for disengaging the engagement member from the rack when the trigger member is displaced to the second position, and for reengaging the engagement member with the rack when the trigger member is returned from the second position to the first position.

Further according to the invention, the cam means preferably includes a rotatable cam member associated with the engagement member and rotatable between an operative position wherein the cam member contacts and disengages the engagement member from the rack and a withdrawn position wherein the cam member is rotated away from contact with the engagement member and the engagement member engages the rack, and cam driving means associated with the handle for rotating the cam means to the withdrawn position when the trigger member is in the first position, and for rotating the cam means to the operative position when the trigger member is in the second position.

The increment of ratchet may advantageously be reduced by providing a ratchet spring for the engagement member which is split and has extending ends of different lengths and/or by providing a rack having notches arranged in a number of side by side arrays wherein the notches of each array are arranged substantially parallel to but out-of-phase with the notches of other arrays.

BRIEF DESCRIPTION OF THE DRAWINGS

A detailed description of the preferred embodiments of the invention follows, with reference to the attached drawings, wherein:

FIG. 1 is a cross-section of a medical instrument with a ratchet assembly according to the invention;

FIG. 3 is a section taken along the lines 3—3 of FIG. 2;

FIG. 11 is a side view of a preferred embodiment of a cam member of the ratchet assembly of the present invention;

FIG. 12 is a section taken along the lines 12—12 of FIG. 11;

FIG. 13 is an end view of the cam means of FIG. 11;

FIG. 17 is a bottom view of a rack for the ratchet assembly according to the invention;

FIG. 18 is a side view of the rack of FIG. 17;

FIG. 19 is a bottom view of an alternate embodiment of the rack; and

FIG. 20 is a side view of the rack of FIG. 19.

DETAILED DESCRIPTION

Figure 4:
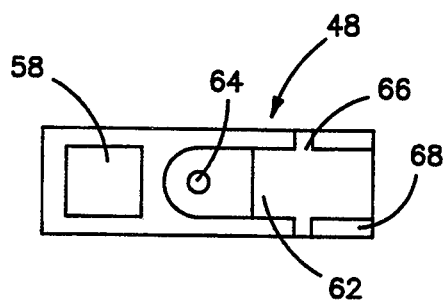
FIG. 4 is a bottom plan view of a carriage member of the ratchet assembly of the present invention.

The present invention relates to a ratchet assembly for medical instruments, especially surgical staples and the like, having a handle and a trigger member movably arranged relative to the handle for operating the instrument.

FIG. 1 shows a cross-section through the relevant portion of a typical medical instrument 10 having a downwardly depending handle 12 and a trigger member 14 pivotably mounted to handle 12 for operation of instrument 10. Trigger member 14 is operatively connected to the operative element of instrument 10, as schematically illustrated at element 16. Element 16 may be a surgical stapler device or any other medical instrument for which a ratchet motion of the trigger is useful. Trigger member 14 is typically pivotable relative to handle 12 around a pivot point 18, and is pivotable between a fully extended position and a fully depressed or pivoted position. A biasing member such as spring 20 is typically provided to bias trigger member 14 towards the fully extended position. Spring 20 is attached within a housing 22 of handle 12 at one end 24, and to trigger member 14 at the other end 26.

According to the invention, a ratchet assembly generally indicated at 28 serves to provide a stepwise pivot of trigger member 14 from the extended position to the fully depressed position. The direction of this pivot is indicated by arrow A. In accordance with the invention, ratchet assembly 28 catches and holds trigger member 14 against spring 20 as trigger member 14 is pivoted in direction A.

Further according to the invention, when trigger 14 has been fully ratcheted or depressed toward handle 12, ratchet assembly 28 operates to disengage, thereby allowing trigger 14 to be returned to the fully extended position by spring 20 for subsequent use.

According to the invention, ratchet assembly 28 includes a rack member 30 fixedly disposed within housing 22, an engagement member 32 slidably disposed relative to rack 30 in the housing, and a cam means 34 associated with engagement member 32 for engaging and disengaging engagement member 32 as will be more fully described below. FIG. 1 shows engagement member 32 disengaged from rack 30, in a position which would allow spring 20 to bias and pivot trigger member 14 in a direction opposite to that indicated by arrow A, to a fully extended position.

Figure 2:
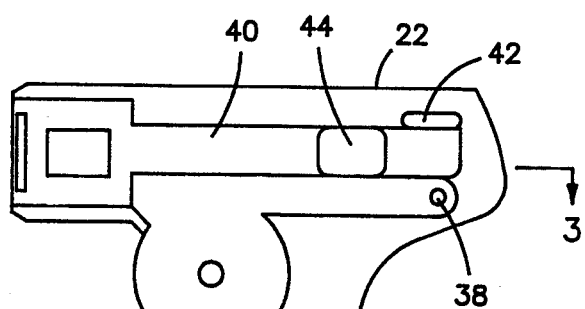
FIG. 2 is a side view of a handle piece for the medical instrument of FIG. 1.

FIG. 2 illustrates an inside view of handle 12 and housing 22. Handle 12 and housing 22 preferably include two sides or halves which are assembled around the relevant interior structure. The inside of one side or half of housing 22 is illustrated in FIG. 2. As shown, handle 12 has a receiving portion 36 for pivotably receiving trigger member 14. A post 38 is provided for attachment of one end 24 of spring 20. (See also FIG. 1). A track 40 is preferably provided within housing 22 to provide slidable mounting of engagement member 32. A recess 42 is also provided to fixedly hold rack 30. Housing 22 also includes a groove 44 into which a portion of cam member 34 is disposed. Upon operation of trigger member 14, groove 44 serves to drive cam member 34 at the limits of motion of trigger 14 so as to provide the desired engagement and disengagement of ratchet assembly 28.

FIG. 3 is a sectional view along lines 3—3 of FIG. 2 which further illustrates the aforementioned features of housing 22.

Returning to FIG. 1, engagement member 32 preferably includes a ratchet spring 46 mounted to a slidable carriage 48. Carriage 48 is slidably disposed within housing 22, preferably in track 40 thereof. Ratchet spring 46 preferably has one end 50 attached to carriage 48, and another extending or operative end 52 which is arranged for operative engagement with rack 30. Ratchet spring 46 has a bend or bias which urges extending end 52 into contact with rack 30. Cam member 34 serves to disengage ratchet spring 46 from rack 30, against the bias of ratchet spring 46, when trigger 14 is fully depressed so that trigger 14 can be biased back to the starting fully extended position. FIG. 1 shows the disengaged position of ratchet spring 46. The operation of this structure is thoroughly discussed below with reference to FIGS. 14–16.

Still referring to FIG. 1, trigger member 14 has a trigger portion 54 extending in one direction from pivot point 18, preferably roughly parallel to downwardly depending handle 12. A reaction portion 56 also extends from pivot point 18 for connection to carriage 48. As shown, carriage 48 preferably has an open receiving area 58 into which reaction portion 56 extends as shown. In this manner, trigger member 14 and carriage 48 are operatively connected so that pivot of trigger member 14 results in translation or sliding of carriage 48 and, thus, ratchet spring 46, relative to rack 30. A post 60 may also preferably be provided on trigger member 14, for example on reaction portion 56, for attachment of end 26 of spring 20 as shown.

Figure 5:
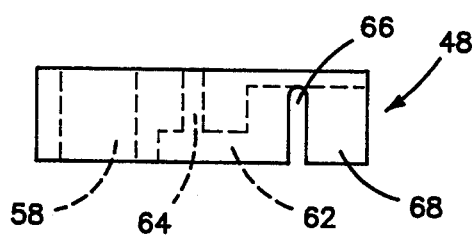
FIG. 5 is a side view of the carriage member of FIG. 4.

FIGS. 4 and 5 illustrate bottom and side views of carriage 48. Receiving area 58 is defined on carriage 48 as shown for receiving reaction portion 56 of trigger 14. Of course, any type of pivotable connection of trigger member 14 to carriage 48 which translates the pivot or lever-like motion of trigger member 14 into sliding of carriage 48 would be suitable in accordance with the invention. Furthermore, it should be appreciated that the trigger member may be of numerous configurations and need not pivot relative to the handle portion of the instrument. For example, the trigger could be a slide trigger or button or the like which is slidably displaced relative to the handle. Such a trigger member would be linked to carriage 48 in any manner suitable to provide the desired motion of carriage 48 responsive to displacement of the trigger.

Carriage 48 preferably includes a recessed area 62 for receiving end 50 of ratchet spring 46. End 50 may be fastened in recessed area by a pin, post or rivet (not shown) which may pass through hole 64. Of course, any of numerous methods may be used for attaching end 50 of ratchet spring 46 to carriage 48 such as glues or adhesives, a press or snap fit, clips or the like. Carriage 48 may be made from plastic, metal such as aluminum or the like, or any other desirable and suitable material. If carriage 48 is to be plastic, then ratchet spring 46 could also be affixed to carriage 48 through a heat staking process wherein spring 46 is attached to the plastic material through the application of heat or sonic welding, or the like.

Carriage 48 also preferably includes a groove 66 formed in a side wall 68 thereof for pivotably receiving cam member 34 (not shown in FIGS. 4 and 5).

Carriage 48 is slidably held in housing 22 by track 40 which is sized to snugly receive carriage 48 to prevent wobble or deflection of the carriage during sliding. The slidable mounting of carriage 48 may be achieved through any other means desirable which may include, for example, flanges in grooves, runners, guides, rollers or the like.

FIGS. 6–10 illustrate various embodiments of ratchet spring 46.

Figure 6:
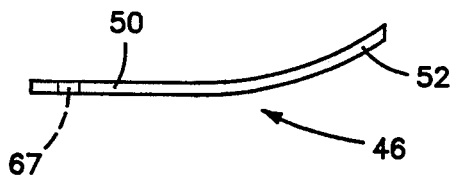
FIG. 6 is a side view of a ratchet spring, according to the invention.

FIG. 6 shows the simplest embodiment of ratchet spring 46 having end 50 for attachment to carriage 48, extending end 52 for engagement with rack 30, and a cutout 67 through which a fastener may be disposed (not shown) for attachment of ratchet spring 46 to carriage 48 at hole 64. When attached to carriage 48, extending end 52 extends beyond carriage 48 and towards rack 30 for engagement therewith.

Figure 7:
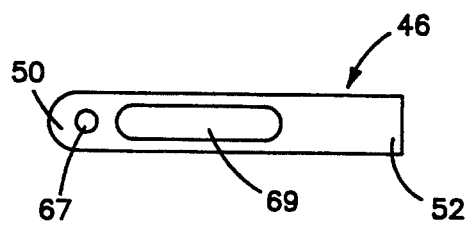
FIG. 7 is a bottom view of an embodiment of the ratchet spring of FIG. 6.

FIG. 7 shows a bottom view of an embodiment of ratchet spring 46 wherein a cutout 69 may be formed in the body of ratchet spring 46 to reduce the spring force of the spring if desired.

Figure 8:
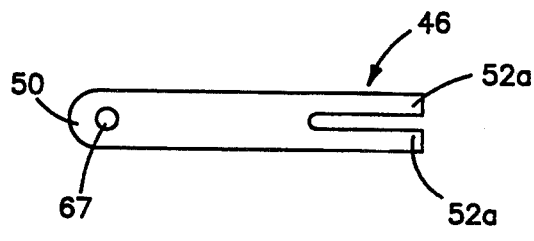

FIG. 8 illustrates an embodiment of ratchet spring 46 wherein end 52 is split to define two extending ends 52a which may be used to interact with a rack 30 having two separate engagement surfaces as will be further described below.

Figure 9:
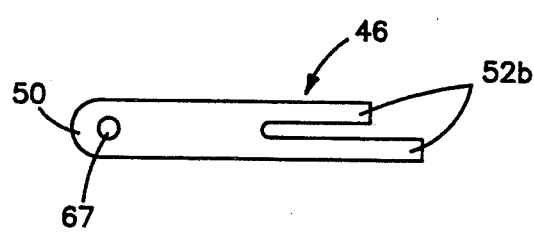
FIGS. 8 and 9 are bottom views of alternate embodiments of the ratchet spring, according to the invention.
Figure 10:
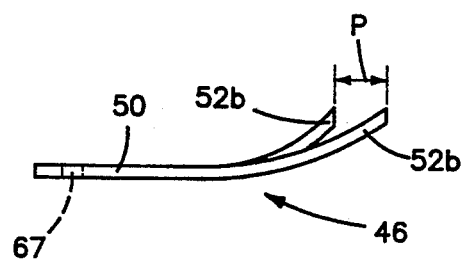
FIG. 10 is a side view of the ratchet spring of FIG. 9.

FIGS. 9 and 10 illustrate an alternate embodiment wherein end 52 is split into two extending ends 52b of different lengths to contact rack 30 in different locations. Ends 52b (See FIG. 10) are preferably spaced at a distance "p" of about ½ of the pitch of notches 70 of rack 30 as discussed below. This is useful in providing small increments of ratchet of the device without having to provide ultra fine grooves or notches on rack 30. Ends 52b alternatingly ratchet from notch to notch on rack 30 in this embodiment.

FIGS. 17–20 illustrate various embodiments of rack 30 which may be used in conjunction with the ratchet spring embodiments of FIGS. 6–10 to provide the desired ratchet increment of ratchet assembly 28. Rack 30 preferably comprises a generally flat substantially square shaped member fixedly held in recess 42 of housing 22 and having an engagement surface for engaging with engagement member 32.

FIG. 17 illustrates the simplest version of rack 30 wherein a plurality of notches 70 are arranged generally normal to the direction of movement B of engagement member 32 (not shown in FIG. 17) relative to rack 30.

FIG. 18 is a side schematic view of the rack 30 of FIG. 17. As shown, notches 70 are defined by a plurality of teeth 72 which are preferably offset or skewed in a direction C which corresponds to the direction of movement of engagement member 32 when trigger member 14 is displaced toward handle 12. In this manner, teeth 72 readily allow ratchet motion of end 52 of ratchet spring 46 from notch to notch in direction C, as is desired. Teeth 72 also serve to firmly hold end 52 of ratchet spring 46 in place against movement opposite to direction C, also as desired. In this way, trigger member 14 is firmly held in place against the bias of spring 20 in a desired position to which it has been ratcheted during movement of trigger member 14 from a fully extended position to a fully depressed position.

FIGS. 19 and 20 illustrate an alternate embodiment of rack 30 having two arrays 74 of notches 70 arranged in side by side fashion, with notches 70 of each array 74 arranged substantially parallel but out-of-phase, preferably by about ½ pitch, with notches of other arrays 74, as shown. Such an embodiment is particularly useful with a ratchet spring 46 as shown in FIG. 8. Ends 52a of ratchet spring 46 alternatingly or intermittently engage with notches 70 of alternating arrays 74 so that a small degree or increment of ratchet can be obtain with teeth 72 defining notches having a large size. FIG. 20 shows a side view of such a rack to illustrate the out-of-phase relationship between teeth 72 of each array 74. FIG. 20 shows teeth 72 having the same pitch in each array, with teeth 72 of one array being ½ pitch out-of-phase with teeth 72 of the other array. Thus, distance "P" in FIG. 20 is equal to about ½ pitch of teeth 72. The pitch between teeth of each array could, of course, be altered so as to provide any particular degree of ratchet which may be desired. Any number of arrays may be provided along with any number of extending end portions 52, 52a, 52b of ratchet spring 46. In this manner, the pitch and relationship of notches 70 of each array may be manipulated in numerous ways to provide a wide variety of types of ratchet of the mechanism, all in accordance with the invention.

FIGS. 11–13 illustrate a preferred embodiment of cam member 34. As set forth above, cam member 34 serves to engage and disengage engagement member 32 with rack 30.

Cam member 34 is preferably a generally elongated shaft having a cam portion 76 and ends 78. At least one end 78, and preferably both ends 78, are formed as a generally cam shaped member to serve as a driven portion of cam member 34 which is acted upon by groove 44 of housing 22 to provide proper operation of cam member 34.

Cam member 34 is rotatably disposed in carriage 48, preferably in groove 66 thereof (see FIGS. 4 and 5). In this regard, cam member 34 has axle portions 80 which are sized for rotatable positioning in groove 66. As shown by the hidden lines of FIGS. 12 and 13, axle portions 80 are preferably generally tear-drop shaped. The rounded portion 82 of the tear-drop sits in the rounded portion of groove 66 of carriage 48 while the flat portions 84 serve to define limits of rotation of cam member 34 in groove 66 to ensure proper rotational positioning thereof.

Cam member 34 is rotatably positionable in groove 66 between an extending or operative position (see FIG. 15, described below) wherein cam portion 76 is oriented to deflect ratchet spring 46 away from and out of engagement with rack 30, and a withdrawn position (see FIGS. 14 and/or 16, also described below), wherein ratchet spring 46 is not deflected and therefore is biased into engagement with rack 30. In this regard, FIG. 12 illustrates a cross-section taken through cam portion 76. As shown, cam portion 76 has two cam surfaces 86, 88 arranged respectively to extend distances a, b from the pivot at rounded portion 82 of axle 80. Cam surface 86 is arranged to extend a distance "a" sufficient, when surface 86 is brought to bear on ratchet spring 46, to deflect ratchet spring 46 away from rack 30. Cam surface 86 is brought to bear when cam 34 is in the aforementioned operative position. Cam surface 88 is arranged to extend a distance "b" which is sufficiently small so that surface 88 does not deflect ratchet spring 46 away from rack 30 when cam member 34 is pivoted to cause cam surface 88 to face ratchet spring 46. Cam surface 88 faces ratchet spring 46 when cam member 34 is in the aforementioned withdrawn position.

Ends 78, as set forth previously, extend through grooves 66 of walls of carriage 48 and into groove 44 of housing 22 (see FIGS. 2 and 3). Ends 78 have a shape which causes pivot of cam member 34 between the operative and the withdrawn position when end 78 contacts end portions 90 of groove 44 (See FIGS. 14, 15 and 16). Ends 78 preferably have a generally wedge shape which may be similar to that of cam portion 76 except that ends 78 do not need surfaces defined at different distances from rounded portion 82 of axle 80. For example, FIG. 13 illustrates surfaces defined at the same distance c from rounded portion 82. The preferred embodiment illustrated in FIG. 13 shows an end view of cam member 34 and end 78 which acts as a driven end, driven by groove 44, to provide the desired pivot of cam member 34.

Figure 14:
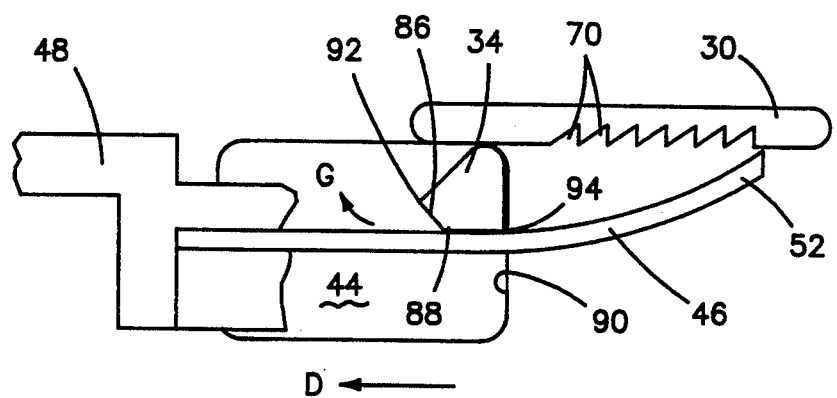
FIGS. 14–16 show various steps of the operation of elements of the ratchet assembly of FIG. 1.
Figure 15:
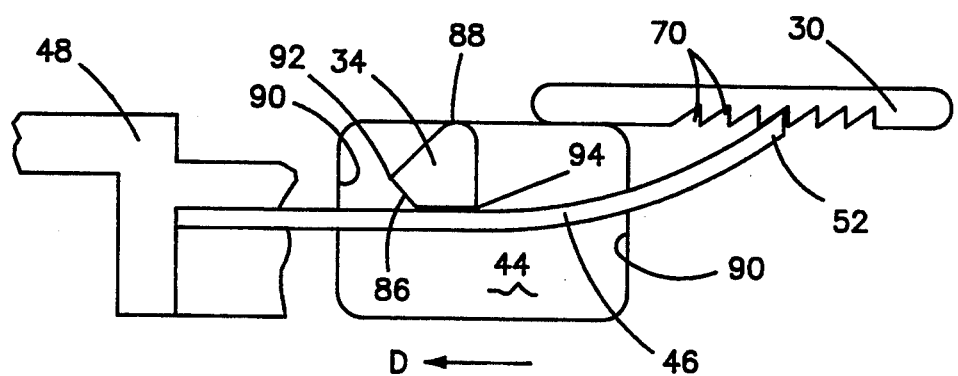
Figure 16:
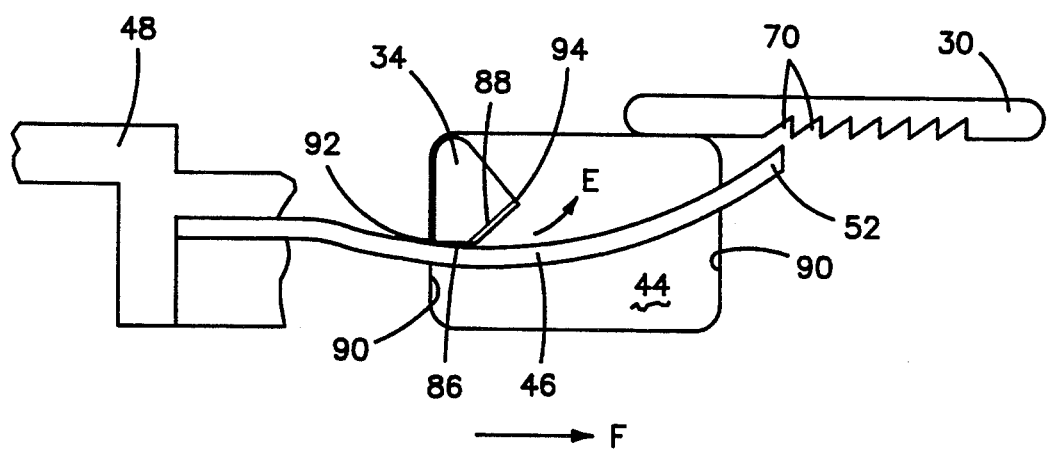

FIGS. 14–16 illustrate the operative elements of ratchet assembly 28 which serve to engage and disengage engagement member 32, particularly ratchet spring 46, as desired. As set forth above, it is desired to provide ratchet movement of trigger member 14 toward handle 12. Once trigger member 14 is fully depressed toward handle 12, it is desired to allow trigger member 14 to return freely to a fully extended position, where it can again be ratcheted back towards handle 12. In this regard, trigger member 14 is connected to carriage 48 and, thus, the operative elements of ratchet assembly 28, via reaction portion 56 of trigger member 14 and receiving area 58 of carriage 48 (as shown in FIG. 1). Thus, a pivot of trigger member 14 toward handle 12 biases carriage 48 to the left as viewed in FIGS. 14–16. In accordance with the invention, cam member 34 preferably serves to engage ratchet spring 46 with rack 30 when trigger member 14 is fully extended away from handle 12, and carriage 48 and associated cam member 34 and ratchet spring 46 are disposed all the way to the right relative to housing 22 and associated rack 30 and groove 44 as viewed, for example, in FIG. 14. From this position, trigger member 14 can be ratcheted through various desired positions in the direction of arrow D until eventually reaching a fully depressed position relative to handle 12. FIG. 15 illustrates an intermediate position corresponding to a partial pivot of trigger 14 toward handle 12. When trigger member 14 is fully depressed toward handle 12, carriage 48 with associated cam member 34 and ratchet spring 46 are disposed all the way to the left relative to housing 22 and associated rack 30 and groove 44 as viewed, for example, in FIG. 16. Upon reaching this position, cam member 34 is pivoted in the direction of arrow E to the orientation shown in FIG. 16, to disengage ratchet spring 46 from rack 30. This allows trigger member 14 to return to the fully extended position, where cam member 34 is again rotated or pivoted to again allow ratchet spring 46 to engage rack 30, and so forth.

Ratchet assembly 28 operates as follows. FIG. 14 illustrates a starting position of cam member 34 relative to groove 44 and ratchet spring 46 relative to rack 30, which corresponds to a fully extended position of trigger member 14. Cam member 34 is arranged, in this position, with cam surface 88 of cam portion 76 facing ratchet spring 46, so that ratchet spring 46 is not deflected away from rack 30. As trigger member 14 is depressed, carriage 48 slides in the direction of arrow D in FIGS. 14 and 15 with end 52 of ratchet spring 46 ratcheting from notch to notch of rack 30. An intermediate position is illustrated in FIG. 15, wherein ratchet spring 46 is engaged in notch 70 to hold trigger member 14 in a desired position against the pull of spring 20 which would otherwise tend to pull carriage 48, and ratchet spring 46 and cam member 34, in a direction opposite to arrow D. When trigger member 14 is fully depressed, cam member 34 reaches an end 90 of groove 44. End 90 contacts point 92 of cam member 34 and pivots the cam member as shown by arrow E in FIG. 16 to bring cam surface 86 of cam portion 76 to bear upon ratchet spring 46, thereby disengaging ratchet spring 46 from rack 30 and allowing spring 20 to bias trigger member 14 back to the fully extended position, with carriage 48 and ratchet spring 46 and cam member 34 moving in direction F to the point shown in FIG. 14 where point 94 of cam member 34 contacts the other end 90 of groove 44 thereby pivoting cam member 34 in direction G to withdraw cam surface 86 from contact with ratchet spring 46 and thereby allow ratchet spring 46 to again engage rack 30 for the next ratcheting movement of trigger member 14 toward handle 12. In this manner, ratchet assembly 28 allows trigger member 14 to be repeatedly ratcheted toward handle 12 and returned to the fully extended position as desired.

Thus disclosed is a ratchet assembly which is useful for providing a ratchet movement of the trigger member of an instrument relative to the handle thereof, and a free return of the trigger member to the starting position. The device of the present invention is simple in manufacture and reliable in use.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A ratchet assembly for a medical instrument having a handle and a trigger member for operating the medical instrument, the trigger member being movable relative to the handle between a first position and a second position and being biased by biasing means toward the first position, the ratchet assembly comprising:

rack member disposed in the handle;

an engagement member for engaging the rack means, slidably disposed in the handle relative to the rack means and connected to the trigger member so that displacement of the trigger member slides the engagement member relative to the rack member, the engagement member being biased into engagement with the rack means so that, as the trigger is displaced from the first position to the second position, the engagement member engages the rack member in a plurality of positions so as to hold the trigger member at a desired point between the first position and the second position against the biasing means; and cam means, arranged in the handle, for disengaging the engagement member from the rack means when the trigger member is displaced to the second position, and for reengaging the engagement member with the rack means when the trigger member is returned to the first position from the second position, said cam means comprising a rotatable cam member associated with the engagement member and rotatable between an operative position wherein the cam member contacts and disengages the engagement member from the rack means and a withdrawn position wherein the cam member is rotated away from contact with the engagement member and the engagement member engages the rack means; and cam driving member associated with the handle for rotating the cam member to the withdrawn position when the trigger member is in the first position, and for rotating the cam member to the operative position when the trigger member is in the second position.

2. A ratchet assembly according to claim 1, wherein the handle is a generally downwardly depending handle depending from a body portion of the instrument, and the trigger member is a trigger pivotably attached to the handle so that the trigger is pivotable between the first position wherein the trigger is pivoted away from the handle, and the second position wherein the trigger is pivoted toward the handle, and wherein the biasing member biases the trigger away from the handle towards the first position, whereby the ratchet assembly incrementally engages to hold the trigger in a desired position along a path from the first position to the second position.

3. A ratchet assembly according to claim 1, wherein the rack member comprises a generally flat rack having an engagement surface for engaging the engagement member in a plurality of positions corresponding to positions of the trigger member between the first position of the trigger member and the second position of the trigger member.

4. A ratchet assembly according to claim 3, wherein the engagement surface comprises an array of notches arranged normal to a path of movement of the engagement member relative to the rack member.

5. A ratchet assembly according to claim 4, wherein the notches are defined by a plurality of teeth which are skewed in a direction of movement of the engagement member relative to the rack means when the trigger member is moved from the first position to the second position, whereby the engagement member readily ratchets from notch to notch as the trigger member is moved to the desired position along a path from the first position to the second position, and whereby the engagement member is firmly engaged to prevent movement of the trigger member back toward the first position from the desired position.

6. A ratchet assembly according to claim 5, wherein the engagement surface comprises a plurality of side by side arrays of notches, wherein the notches of each array are arranged out-of-phase with the notches of other arrays of the plurality of arrays whereby the engagement member ratchets cyclically through notches of each array as the trigger is moved to the desired position along the path from the first position to the second position.

7. A ratchet assembly according to claim 6, wherein the notches of each array are arranged out-of-phase by a distance of ½ of a pitch of the notches.

8. A ratchet assembly according to claim 1, wherein the engagement member includes a ratchet spring slidably mounted relative to the rack member in the handle and having a first end associated with the trigger member and a second end biased into contact with the rack member.

9. A ratchet assembly according to claim 8, wherein the ratchet spring is mounted at the first end to a carriage slidably mounted in the housing and wherein the carriage is operatively connected to the trigger member.

10. A ratchet assembly according to claim 9, wherein the trigger member is pivotably mounted to the handle at a pivot point and has a trigger portion extending in one direction from the pivot point and a reaction portion extending in another direction from the pivot point for engagement with the carriage, whereby pivot of the trigger member is translated into sliding of the carriage and ratchet spring relative to the rack means.

11. A ratchet assembly according to claim 1, wherein the cam member includes a cam face positioned on the cam member at a distance from a pivot point of the cam member which is sufficient to disengage the engagement member from the rack member when the cam member is in the operative position.

12. A ratchet assembly according to claim 11, wherein the cam driving member includes a groove formed in the handle generally following a direction of movement of the engagement member relative to the rack means and wherein the cam member has a driven end disposed in the groove of the driving means and contoured so that ends of the groove rotate the cam member between the operative position and the withdrawn position.

13. A ratchet assembly according to claim 12, wherein the driven end has a first driven member and a second driven member extending in different directions from the pivot point so that, when the first driven member contacts a first end of the groove, the cam member is rotated so that the second driven member is positioned for driving by a second end of the groove, the first and second ends of the groove corresponding to the position of the cam member relative to the groove when the trigger member is in the first and second positions respectively.

14. A ratchet assembly according to claim 13, wherein the engagement member includes a sliding carriage slidably mounted relative to the rack member within the handle, and wherein the cam member is rotatably mounted in the carriage.

15. A ratchet assembly according to claim 14, wherein the end of the cam member laterally extends through the carriage into the groove of the cam driving means.

16. A ratchet assembly for a medical instrument having a handle and a trigger member for operating the medical instrument, the trigger member being movable relative to the handle between a first position and a second position and being biased by biasing member toward the first position, the ratchet assembly comprising:

rack member disposed in the handle;
an engagement member for engaging the rack means, slidably disposed in the handle relative to the rack means and connected to the trigger member so that displacement of the trigger member slides the engagement member relative to the rack means, the engagement member being biased into engagement with the rack means so that, as the trigger is displaced from the first position to the second position, the engagement member engages the rack means in a plurality of positions so as to hold the trigger member at a desired point between the first position and the second position against the biasing means and wherein the engagement member includes a ratchet leaf spring slidably mounted relative to the rack means in the handle and having a first end associated with the trigger member and a second end biased into contact with the rack means, and wherein the ratchet leaf spring includes at least one slot formed on the ratchet leaf spring to define at least two ratchet leaf spring elements and wherein the at least two ratchet leaf spring elements have different lengths so as to contact the rack means at different locations; and
cam means, arranged in the handle, for disengaging the engagement member from the rack means when the trigger member is displaced to the second position, and for reengaging the engagement member with the rack means when the trigger member is returned to the first position from the second position.

17. A ratchet assembly according to claim 16, wherein the rack means comprises a generally flat rack having an engagement surface for engaging the engagement means in a plurality of positions corresponding to positions between the first position of the trigger and the second position of the trigger, and wherein the engagement surface comprises an array of notches arranged normal to a path of movement of the engagement member relative to the rack means, whereby the at least two ratchet leaf spring elements of the engagement member alternatingly engage from notch to notch of the engagement surface as the trigger member is moved from the first position to the second position.

18. A ratchet assembly according to claim 16, wherein the at least two ratchet leaf spring elements intermittently contact the rack means at different locations.

* * * * *

UNITED STATES PATENT AND TRADEMARK OFFICE
CERTIFICATE OF CORRECTION

PATENT NO. : 5,344,061

DATED : September 6, 1994

INVENTOR(S) : Lawrence Crainich

It is certified that error appears in the above-identified patent and that said Letters Patent is hereby corrected as shown below:

In Column 5, line 56, "obtain" should read --obtained--.

In Column 8, claim 1, line 27, "member" should read --means--.

In Column 8, claim 1, line 32, "member" (second occ.) should read --means--

In Column 8, claim 1, line 37, "member" should read --means--.

In Column 8, claim 1, line 55, "member" should read --means--.

In Column 9, claim 3, line 7, "member" should read --means--.

In Column 9, claim 8, line 43, "member" should read --means--.

In Column 9, claim 8, line 46, "member" should read --means--.

In Column 9, claim 11, line 64, "member" (second occ.) should read --means

In Column 9, claim 12, line 67, "member" should read --means--.

In Column 10, claim 14, line 20, "member" should read --means--.

In Column 10, claim 16, line 31, "member" should read --means--.

In Column 10, claim 16, line 34, "member" should read --means--.

UNITED STATES PATENT AND TRADEMARK OFFICE
CERTIFICATE OF CORRECTION

PATENT NO. : 5,344,061
DATED : September 6, 1994
INVENTOR(S) : Lawrence Crainich It is certified that error appears in the above-indentified patent and that said Letters Patent is hereby corrected as shown below:

In Column 10, claim 16, line 34, "member" should read --means--.

Signed and Sealed this

Fourteenth Day of February, 1995

Attest:

BRUCE LEHMAN

Attesting Officer     Commissioner of Patents and Trademarks